US005891338A

United States Patent [19]
Bell et al.

[11] Patent Number: 5,891,338
[45] Date of Patent: Apr. 6, 1999

[54] HEAT-STERILIZABLE MEMBRANE

[75] Inventors: Carl-Martin Bell, Hechingen; Reinhold Buck, Alleshausen; Barbara Thome, Filderstadt; Markus Storr, Leinfelden-Echterdingen; Hermann Gohl, Bisingen, all of Germany

[73] Assignee: Gambro Dialysatoren GmbH & Co. KG, Germany

[21] Appl. No.: 632,850

[22] Filed: Apr. 16, 1996

[30] Foreign Application Priority Data

Apr. 20, 1995 [DE] Germany .................. 195 14 540.2

[51] Int. Cl.$^6$ .................................................. B01D 39/00
[52] U.S. Cl. ............................... 210/500.32; 210/500.29; 210/500.38; 210/500.39; 210/500.4; 210/500.41; 210/500.42
[58] Field of Search ................. 210/500.38, 500.29, 210/500.32, 500.41, 500.43, 500.39, 500.4, 500.42

[56] References Cited

U.S. PATENT DOCUMENTS

| | | |
|---|---|---|
| 4,069,151 | 1/1978 | Higley et al. . |
| 4,276,137 | 6/1981 | Hovel et al. ............................ 204/164 |
| 4,545,910 | 10/1985 | Marze ...................................... 210/651 |
| 4,935,141 | 6/1990 | Buck et al. ........................ 210/500.43 |
| 4,975,190 | 12/1990 | Sakashita et al. ................ 210/500.38 |
| 5,205,968 | 4/1993 | Damrow et al. .................. 210/500.41 |
| 5,308,489 | 5/1994 | Dhein et al. ...................... 210/508.38 |
| 5,505,851 | 4/1996 | Wagener et al. ....................... 210/490 |

FOREIGN PATENT DOCUMENTS

| | | |
|---|---|---|
| 0001879 | 5/1979 | European Pat. Off. . |
| 0 228 072 | 7/1987 | European Pat. Off. . |
| 0 305 787 | 3/1989 | European Pat. Off. . |
| 0337626 | 10/1989 | European Pat. Off. . |
| 0 604 882 | 7/1994 | European Pat. Off. . |
| 43 25 650 C1 | 9/1994 | Germany . |

OTHER PUBLICATIONS

Hakim et al., "Effect of the Dialysis Membrane in the Treatment of Patients with Acute Renal Failure," The New England Journal of Medicine, vol. 331, No. 20, Nov. 17, 1994, pp. 1338–1342.

Hakim et al., "Complement Activation and Hypersensitivity Reactions to Dialysis Membranes," The New England Journal of Medicine, vol. 331, No. 14, Oct. 4, 1984, pp. 878–882.

Schiffl et al., "Biocompatible membranes in acute renal failure: prospective case–controlled study," The Lancet, vol. 344, Aug. 27, 1994., pp. 570–572

Wegmuller et al. "Biocompatibility of different hemodialysis membranes: activation of complement and leukopenia," The International Journal of Artificial Organs, vol. 9 No. 2, 1986, pp. 85–92.

"Polyamide—The Evolution of a Synthetic Membrane for Renal Therapy," ed. S. Shaldon, K. M. Koch, Contributions to Nephrology, vol. 96, Karger [1992].

*Primary Examiner*—Ana Fortuna
*Attorney, Agent, or Firm*—Lerner, David, Littenberg, Krumholz & Mentlik, LLP

[57] ABSTRACT

Heat-sterilizable membranes are disclosed comprising at least two hydrophobic polymers which are normally immiscible with each other, and in which at least one of the hydrophobic polymers is normally unstable under sterilization conditions while at least one of the other hydrophobic polymers is normally stable at sterilization conditions, and in which the at least two hydrophobic polymers are compatibilized with each other so that the membrane formed therefrom is stable at such sterilization conditions.

20 Claims, No Drawings

HEAT-STERILIZABLE MEMBRANE

FIELD OF THE INVENTION

The present invention relates to permselective membranes. More particularly, the present invention relates to such membranes which can be used in connection with medical treatments such as hemodialysis, hemofiltration, hemodiafiltration, plasmapheresis, or immunotherapy. Still more particularly, the present invention relates to such membranes which can also be used for dialysis or ultrafiltration in general, such as for the purification of water and the like.

BACKGROUND OF THE INVENTION

One important requirement for rendering it possible to use membranes in medical procedures, such as in blood purification therapy, is that the membranes are capable of being sterilized. For reasons relating both to safety and environmental protection, and which relate to the production of by-products and toxic residues, steam sterilization or sterilization using dry heat are preferred over such sterilization procedures as the use of ethylene oxide gas, the use of plasma processes, such as with hydrogen peroxide, or the use of irradiation, such as with γ-rays.

Sterilization with steam is usually effected by treating the membrane for a period of about 20 minutes with saturated steam at a temperature of about 120° C. Sterilization with dry heat is usually effected for a period of about 90 minutes at 180° C. (DAB 1992). Those sterilization conditions, however, result in a limitation of the number of synthetic polymers which can be used for that purpose. Thus, for example, dialysis membranes of polyacrylonitrile (U.S. Pat. No. 4,545,910), cellulose triacetate (U.S. Pat. No. 4,276,137) and partially aromatic amorphous polyamide (laid-open European Patent Application No. 305,787) cannot be sterilized with steam, because an irreversible and disadvantageous change in the pore structure occurs under these steam sterilization conditions. Hydrolysis-sensitive polymers such as poly-(carbonate block ethylene oxide) (U.S. Pat. No. 4,069,151) also cannot be sterilized with steam, since in this case the polymer would be decomposed, resulting in breaks or holes in the membrane. In addition, those membranes are impregnated with hydrophilizing agents, such as with polyvinylpyrrolidone, glycerin or polyethylene glycol (laid-open European Patent Application No. 228,072) which further increases the instability of these membrane structures by heating, as a result of the softening effect of these materials.

On the other hand, it is precisely such dialysis membranes consisting of those polymers which possess unusually good hemocompatibility in comparison with dialysis membranes of the cellulose type (see "Polyamide—the Evolution of a Synthetic Membrane for Renal Therapy", edited by S. Shaldon, K. M. Koch in *Contributions to Nephrology*, volume 96, Karger [1992]; E. Wegmüller, A. Montandon, "Biocompatibility of Different Hemodialysis Membranes, Activation of Complement and Leukopenia," *Inte. J. Artif. Organs*, 9, 85 [1986]; R. M. Hakim et al., "Complement Activation and Hypersensitivity Reactions to Dialysis Membranes", *New England J. Med.*, 311, 878 [1984]; H. Schiffl, "Biocompatible Membranes in Acute Renal Failure, Prospective Casecontrolled Study," *Lancet*, 344, 570 [1994]; and R. M. Hakim et al., "Effect of the Dialysis Membrane in the Treatment of Patients with Acute Renal Failure," *New England J. Med.*, 311, 1338 [1994].

Furthermore, partially aromatic amorphous polyamides in particular have a particularly high endotoxin or pyrogen retention capacity. See the discussion in Lonnemann et al., "Pyrogen Retention by the Polyamide Membrane," in "Polyamide—The Evolution of a Synthetic Membrane for Renal Therapy," edited by S. Shaldon, K. M. Koch, *Contributions to Nephrology*, 96, 47 (1992), relating to the high level of efficiency of asymmetrical polyamide membranes with respect to endotoxin retention capacity, and which attributes crucial significance to the interaction of the pyrogenic bacterial substances with the hydrophobic domains of the membrane, which are formed by polyamides.

Laid-open European Patent Application No. 604,882 describes a semipermeable membrane comprising sulphonated aromatic polyetherketone and fully aromatic polyamide, possibly with the addition of polyvinylpyrrolidone. These two polymers are thermally stable under the conditions of steam sterilization, so that it is not surprising that such a membrane is sterilizable with steam.

It is therefore an object of the present invention to provide a membrane which can be sterilized with heat, and in particular with steam, while also using a polymer, such as a polyamide or polyvinylpyrrolidone, which is unstable under the usual conditions of sterilization with steam or dry heat, that is to say with saturated steam and at a temperature of about 120° C.

SUMMARY OF THE INVENTION

In accordance with the present invention, these and other objects have now been realized by the invention of a heat-sterilizable membrane comprising a first hydrophobic polymer and a second hydrophobic polymer, the first and second hydrophobic polymers normally being immiscible with each other, the first hydrophobic polymer normally being unstable when subjected to sterilization conditions comprising contact with saturated steam at about 120° C. for a period of about 20 minutes or contact with dry heat at about 180° C. for a period of about 90 minutes, and the second hydrophobic polymer normally being stable at the sterilization conditions, the first and second hydrophobic polymers being compatibilized with each other whereby the heat-sterilizable membrane is stable at these sterilization conditions.

In accordance with one embodiment of the heat-sterilizable membrane of the present invention, the first and second hydrophobic polymers are compatibilized by being covalently bonded to each other.

In accordance with another embodiment of the heat-sterilizable membrane of the present invention, the first hydrophobic polymer is present in the membrane in an amount of from about 1 to 30% by weight, and preferably in an amount of from about 4 to 12% by weight, and the second hydrophobic polymer is present in the membrane in an amount of from about 70 to 99% by weight, and preferably in an amount from about 88 to 96% by weight.

In accordance with another embodiment of the heat-sterilizable membrane of the present invention, the second hydrophobic polymer has a vitreous transition temperature ($T_g$) of greater than about 200° C.

In accordance with another embodiment of heat-sterilizable membrane of the present invention, the first hydrophobic polymer is selected from the group consisting of partially aromatic polyamides, polycarbonate ethers, polyacrylonitriles, and cellulose triacetates, and preferably partially aromatic amorphous polyamides.

In accordance with another embodiment of the heat-sterilizable membranes of the present invention, the second hydrophobic polymer is selected from the group consisting of polyethersulfones, polysulphones, polyetherketones, and polyaramides, and preferably polyethersulfones and polysulphones.

In accordance with another embodiment of the heat-sterilizable membrane of the present invention, the first and second hydrophobic polymers are present in a molecular distribution of a particle size of up to about 1 µm.

In accordance with another embodiment of the heat-sterilizable membranes of the present invention, the first and second hydrophobic polymers are compatibilized with each other by means of an amphiphilic agent, and preferably in which the amphiphilic agent is present in an amount of between about 5 and 10% by weight.

In accordance with another embodiment of the heat-sterilizable membrane of the present invention, the first and second hydrophobic polymers are compatibilized with each other by sulphonation of the second hydrophobic polymer under these sterilization conditions. In another embodiment, the first and second hydrophobic polymers are compatibilized with each other by means of polyvinylpyrrolidone.

DETAILED DESCRIPTION

It has surprisingly been found that the membranes according to the present invention are sterilizable with steam or dry heat, even though they contain in part a polymer or polymer component which as such is not normally stable under the usual steam sterilization conditions, and which normally experience disadvantageous changes in terms of their structure under these conditions. On the basis of the principle of the weakest link in a chain, the expectation of those of ordinary skill in this art would have been that the membranes according to the present invention, upon such sterilization with steam or dry heat, would decompose in the regions of the polymer which are unstable in themselves, and as a result the overall membrane would become useless. Surprisingly, however, the polymer which in itself is unstable under the conditions involved in steam sterilization or sterilization with dry heat becomes stable if a polymer which is stable under the specified conditions, using a compatibilization method, is added to or is covalently bonded to the unstable polymer.

The membranes according to the present invention preferably comprise from about 1 to 30% by weight of the at least one polymer which is unstable under such conditions of sterilization, and from about 70 to 80% by weight of the at least one polymer which is stable under such conditions of sterilization. Particularly desirable are membranes comprising from about 4 to 12% by weight of the first (unstable) polymer and about 88 to 96% by weight of the second (stable) polymer.

For the sake of simplicity, the polymers which are unstable at conditions under which sterilization normally operates are hereinafter referred to as the "thermally unstable polymers" and the polymers which are stable under these conditions are referred to as the "thermally stable polymers."

The thermally stable polymers used are preferably such polymers with a vitreous transition temperature ($T_g$) of higher than about 200° C., such as a polyethersulphone, polysulphone, polyetherketone or polyaramide. Polyethersulphones and polysulphones are preferred, and most particularly polyethersulphones.

The thermally unstable polymers are preferably partially aromatic amorphous polyamides, polycarbonate ethers, polyacrylonitriles and cellulose triacetates. A particularly desirable combination, whether it is in the form of a compatibilized mixture or polymers which are covalently bonded to each other, are partially aromatic amorphous polyamides as the thermally unstable polymers, with polyethersulphones as the thermally stable polymers. Polyethersulphones have, for example, repetitive structural units of the formulae which are specified on page 2 of German laid-open Application (DE-OS) No. 42 19 218.

Solutions of two polymers which are not normally miscible with each other frequently separate out into two phases and produce an emulsion in which the more soluble polymer "salts out" the less soluble polymer. By using surface-active agents or other amphiphilic substances, such as block copolymers which have regions of different polarities, it is possible to regulate and stabilize the size of the droplets of the emulsion. Thus, compatibilization of the two hydrophobic polymers which are not miscible or compatible with each other can be achieved by means of an amphiphilic agent. Such an agent is preferably used in an amount of from about 5 to 10% by weight, with respect to the weight of the entire polymers used. When using amphiphilic agents of this type, on the one hand the surface tension is reduced, and on the other hand a mixture with a higher degree of dispersity and an elevated level of adhesion is formed (see R. Fayl, R. Jerome, *ACS Symposium Ser.* 395, 38 [1989]). By virtue of using amphiphilic block copolymers, strong H-bonds are formed on one block and bonds are formed by van der Waals forces on the other block, which result in compatibilization of the two hydrophobic polymers which are not normally miscible with each other per se, thus resulting in mixtures of the two polymers in the molecular range and/or nanometer particle range. Amphiphilic block copolymers which are suitable for this purpose are, for example, poly-(styrene-b-ethylene oxides) in which the polyethylene oxide residue weakens the hydrogen bonding of the polyamide, and the polystyrene residue builds up an interaction with the polyethersulphone molecules.

Alternatively, compatibilization of the two types of polymers can also be effected with other substances which on the one hand have strong H-bonding sites and on the other hand hydrophobic or van der Waals bonding sites, as with ethanol and other alcohols, urea, polyvinylpyrrolidone, ε-caprolactam, organic acids or polyethylene glycol.

Furthermore, compatibilization can also be effected by using bifunctional reactive compounds, such as bisoxazolines or bis-maleic acid imide derivatives, which weaken the intramolecular and intermolecular forces between the two polymer types, such as polyamide and polyethersulphone, and provide for intermolecular adhesion of macromolecules of the two polymer types which are not normally miscible with each other.

C. Mees et al. Describe in *Journal of Polymer Science*, 32 (16, 3171 [1994]) the synthesis of amino terminal group-modified polyether sulphones by a transetherification reaction during polycondensation in the presence of m-aminophenol. These authors then disguise the polyethersulphone with maleic acid anhydride and thus obtain anhydride terminal group-modified polyethersulphones with vitreous transition temperatures of about 270° C.

In "Polymer Bulletin," 29 (5), 477 (1992), S. J. Park describes a copolycondensation operation with amino group-bearing monomers in side groups for the synthesis of amine-functional polyethersulphones. This method makes it possible to adjust the degree of aminization by means of the copolymer component.

Polyamides, for example Trogamid T® (Hüls), have terminal amino groups or carboxyl groups, depending on the respective monomer ratio.

Compatibilization can be achieved by covalent bonding of the polyamide with the described functionalized polyethersulphone modifications, in accordance with the following reactions:

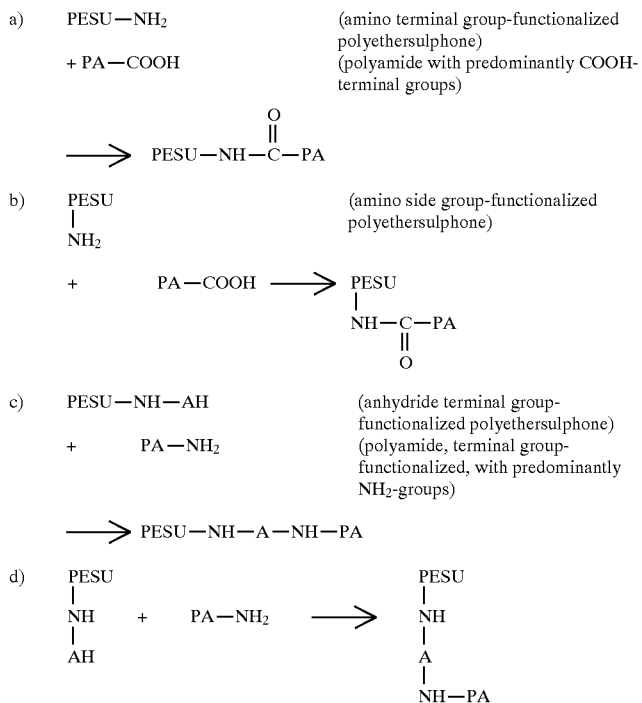

These reactions can be carried out in the molten material, in an extruder, or in an inert solvent at elevated temperatures. The compatibilized copolymers are then spun out of solution to form membranes.

Still another type of compatibilization involves introducing into the thermally stable polymers, such as a polyethersulphone, groups which form strong H-bonds, which permit an interaction with the thermally unstable polymer, such as a polyamide. This can be achieved by a procedure whereby the thermally stable polymers are sulphonated, in which case the degree of sulphonation can be adjusted in accordance with the desired degree of mixing and the desired particle size. Such sulphonated polymer, especially polyethersulphones and polysulphones, are described in German laid-open Application (DE-OS)No. 42 19 218 and the literature referred to therein.

A further method of compatibilizing the two polymer types used herein lies in the use of inorganic fillers, as described in laid-open European Patent Application No. 398,093. Such inorganic fillers include, for example, $TiO_2$, $BaSO_4$ or $SiO_2$ in the form of fine micro- or nanometer particles, which are used in aprotic dipolar solvents. In addition, it is also possible in this situation to use surface-active substances, such as ionic or non-ionic detergents. On the other hand, in salt solutions such as those of lithium chloride or calcium chloride, the intermolecular and intramolecular H-bonds of the thermally unstable macromolecules can be broken down, and such strong interactions can be produced, for example, between sulphone and carbonamide groups of the polyamide, which can result in miscibility in the nanometer range to the molecular range.

Preferably, the compatibilization procedure affords mixtures of the thermally unstable and thermally stable polymers with domain sizes of from about 0.01 to 1 μm.

Arakawa et al. describe the relevance of the domain size in "Artificial Organs," 16 (2), 146 (1992), in regard to the thrombogenity in the case of poly(acrylonitrile-coethyl oxide)-hollow-fiber membrane dialyzers, and find that domain sizes below about 100 nm afford significant improvements in regard to the blood coagulation parameters.

Instead of compatibilization of the two types of polymers in the manner discussed above for producing mixtures of the two types of polymers, they can also be compatibilized by being covalently bonded to each other at their interface, in order to prevent separation of the components of the mixture. This can be achieved by interface reaction of the functionalized polymers (that is to say by way of the terminal groups thereof) with a reactive compatibilization agent. For example, polystyrene can be joined to polyamide by means of the compatibilization agent poly-(styrene)-comaleic acid anhydride, or polyethylene can be joined to polyamide using the compatibilization agent poly-(ethylene maleic acid anhydride).

The membranes in accordance with the present invention may be in sheet or hollow fiber form in the usual manner, and are highly suitable for use in dialysis, blood purification therapy, and/or ultrafiltration.

EXAMPLES

Example 1

Using a round-bottomed flask provided with a thermostat and a polytetrafluoroethylene agitator, a partially aromatic polyamide Trogamid T® (Hüls) was dissolved with vigorous agitation in N-methylpyrrolidone, in the percentages by weight specified in Table I. After complete dissolution the compatibilization agent specified in Table I was added and completely dissolved. Thereafter, polyethersulphone or modified polyethersulphone was added and dissolved, and in the last stage additional additive was possibly added in order to adjust the membrane performance.

The polymer solution thus obtained was filtered through a filter with pore openings of 2 μm and degassed, the viscosity was measured at 22° C. Hollow fiber membranes were produced in the usual manner from the polymer solution, by a procedure whereby the polymer solution was extruded through an annular gap nozzle at the temperature specified in Table I, and was precipitated with the agent solution also specified in Table I. The hollow fiber was drawn from the nozzle at a speed of about 40 to 80 m/min. and passed through a series of rinsing baths. The hollow fibers were then wound up, cut into bundles of a hundred each, dried at 45° C., cast in polyurethane, sterilized with steam and identified. The performance of the hollow-fiber membranes is also specified in Table I. In the columns headed "Polymer solution" and "Agent Solution" the numerical entries denote in each case the percentage content. In Table I, the meanings of the abbreviations are as follows:

Lp1: Hydraulic permeability, measured for pure water ($10^{-4}$ cm/s/bar) in accordance with "Evaluation of Hemodialysis and Dialysis Membranes," NIH-publication 77-1294 [1977].

Lp(Alb): Hydraulic permeability for a 6% cattle albumin solution ($10^{-4}$ cm/s/bar), measured in accordance with the method described in "Evaluation of Hemodialysis and Dialysis Membranes," NIH-publication 77-1294 [1977].

Lp2: Hydraulic permeability for pure water after the Lp-(Alb)-measurement ($10^{-4}$ mc/s/bar) measured in accordance with "Evaluation of Hemodialysis and Dialysis Membranes," NIH-publication 77-1294 [1977].

P(C1): Diffusion permeability for a 0.9% NaCl-solution ($10^4$ cm/sec), measured in accordance with "Evaluation of Hemodialysis and Dialysis Membranes," NIH-publication 77-1294 [1977].

Sk(Myo): Sieve coefficient for a 0.002% myoglobin solution after 15 min. (%), measured in accordance with DIN 58 353, parts 2 C 3, 1988.

Sk(Alb): Sieve coefficient of a 6% cattle albumin solution after 15 min. (%), measured in accordance with DIN 58 353, part 2 C 3, 1988.

TABLE I

Performance of dialysis hollow-fibre membranes of compatibilised polyethersulphone/polyamide alloys

| Polymer solution | | | | | Agent solution | | | Spin. temp. | Visc. (cp) | Lp1 (cm/s. bar. $10^{-4}$) | P(Cl) (cm/s. $10^{-4}$) | Lp(Alb) (c./s. bar. $10^{-4}$) | Lp2 (cm.s. bar. $10^{-4}$) | Sk (Myo) (%) | Sk (Alb) (%) |
|---|---|---|---|---|---|---|---|---|---|---|---|---|---|---|---|
| Polymer 1 | Polymer 2 | Compat. agent | Additive | Solvent | Water | Additive | Solvent | | | | | | | | |
| 14PESU | – | 0.74PA | 2K90 + 5K30 | 2 H₂O – 76.3NMP | 67 H₂O | 1K90 | 42NMP | 50 | 4400 | 174 | 13.2 | 6.3 | 61 | 72 | 6 |
| 14PESU | – | 0.74PA | 2K90 + 4K30 | 2 H₂O – 77.3NMP | 57 H₂O | 1K90 | 4NMP | 50 | 4100 | 132 | 13.7 | 5.9 | 87 | 74 | 17 |
| 13.3PE8 | – | 0.7PA | 2K90 + 5K30 | 0.3 CaCl₂ – 78.7NMP | 55 H₂O | 1-K90 | 44NMP | 50 | 5000 | 181 | 7.8 | 6.9 | 82 | 82 | 37 |
| 12.6PESU | – | 1.4PA | 2K90 + 5K30 | 2 H₂O – 77NMP | 67 H₂O | 1K90 | 42NMP | 50 | 7000 | 84 | 10.7 | 6.6 | 44 | 70 | 28 |
| 12.6PESU | – | 1.4PA | 2K90 + 5K30 | 4 ETOH – 2 H₂O – 73NMP | 67 H₂O | 1K90 | 42NMP | 50 | 6400 | 65 | 10.0 | 8.1 | 35 | 75 | 16 |
| 12.6PESU | – | 1.4PA | 2K90 + 5 K30 | 3 Capro – 76NMP | 57 H₂O | 1K90 | 42NMP | 50 | 8800 | 76 | 9.3 | 6.9 | 54 | 68 | |

PESU: Polyethersulphone Ultrason E 6020, BASF
PES: Polyethersulphone Ultrason E 6010, BASF
PA: Partially aromatic polyamide Trogamid T, Hüls
K30, K90: Polyvinylpyrrolidone of Kollidon type, BASF
NMP: N-Methylpyrrolidone
ETOH: Ethanol
Capro: ε-caprolactam Example 2

Polyethersulphone was sulphonated in accordance with German laid-open Application (DE OS) No. 42 19 218 with 0.7 mmol/g degree of sulphonation. A polymer solution of 13.3% by weight of sulphonated polyethersulphone with 0.7% by weight of polyamide Tragamid T® (Hüls) produces a clear solution in NMP, while the corresponding solution comprising the same non-sulphonated polyethersulphone produces a cloudy polymer solution which cannot be homogeneously mixed. The permeability of wet flat membranes produced from those two polymer solutions, precipitated in water, in accordance with the above-cited patent, is shown in the following Table:

| Solvent Composition | $L_p(H_2O)$ [$10^{-4}$cm/s.bar] | P(Cl) [$10^{-4}$cm/s] |
|---|---|---|
| 13.3% sulphonated polyethersulphone + 0.7% Trogamid T ® | 300 | 12.2 |
| 13.3% polyether-sulphone + 0.7% Trogamid T ® | 240 | <0.5 |

It can thus be seen that sulphonation of the hydrophobic component make it possible to achieve compatibilization with the hydrophilic component.

Example 3

Using a round-bottomed flask provide with a thermostat and with a polytetrafluoroethylene agitator, the partially aromatic polyamide used in Example 1 (Trogamid T®, Hüls) was dissolved in N-methylpyrrolidone with vigorous agitation at 60° C., in the weight percentages specified in Table II. After complete dissolution the compatibilization agent specified in Table II was added and completely dissolved. Thereafter, polyethersulphone and additional additive was added and gradually dissolved.

The polymer solution thus obtained was filtered through a filter with pore openings of 2 μm, degassed, and characterized by viscosity measurement at 22° C. In order to produce hollow fiber the polymer solution was extruded through an annular gap nozzle at the temperature specified in Table II and precipitated with the agent solution also specified in Table II. The hollow fiber was drawn from the nozzle at a speed of between bout 40 and 80 m/min and passed through a series of rinsing baths. The hollow fiber was then wound up, cut to bundles of 100 each, dried at 45° C., cast in polyurethane, sterilized with steam and identified. The performance of the hollow-fiber membranes is also specified in Table II. As the information in this Table shows, the membranes obtained are suitable for use in medium-flow hemodialysis. The abbreviations in this Example bear the same meaning as in Example 1.

TABLE II

| Polymer solution | | | | | Agent solution | | | Spin. temp. | Visc. (cp) | Lp1 (cm/s. bar. $10^{-4}$) | P(Cl) (cm/s. $10^{-4}$) | Lp(Alb) (c./s. bar. $10^{-4}$) | Lp2 (cm.s. bar. $10^{-4}$) | Sk (Myo) (%) | Sk (Alb) (%) |
|---|---|---|---|---|---|---|---|---|---|---|---|---|---|---|---|
| Polymer 1 | Polymer 2 | Compat. agent | Additive | Solvent | Water | Additive | Solvent | | | | | | | | |
| 13.86Pesu – 75NMP | 0.14PA | 4K90 + 5K30 | – | 2 H$_2$O | 75 H$_2$O | 1K90 | 24NMP | 50 | 17964 | 10.4 | 14.7 | 4 | 10.3 | 34.5 | 1.1 |
| 13.85PESU – 2 H$_2$O – 75NMP | 0.14PA | 4K90 + 5K30 | – | | 65 H$_2$O | 1K90 | 34NMP | 40 | 12984 | 12 | 13.3 | 3.7 | 9.9 | 45.9 | 3.4 |
| 13.86PESU – 2 H$_2$O – 77.5NMP | 0.14PA | 4K90 + 3K30 | – | | 90 H$_2$O | 1K90 | 9NMP | 50 | 7701 | 2.4 | 16.1 | 3.9 | 10.1 | 5.7 | |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A heat-sterilizable membrane comprising a first hydrophobic polymer and a second hydrophobic polymer, said first and second hydrophobic polymers normally being immiscible with each other, said first hydrophobic polymer normally being unstable when subjected to sterilization conditions comprising contact with saturated steam at about 120° C. for a period of about 20 minutes or contact with dry heat at about 180° C. for a period of about 90 minutes, and said second hydrophobic polymer normally being stable at said sterilization conditions, said first and second hydrophobic polymers being compatibilized with each other by being covalently bonded to each other whereby said heat-sterilizable membrane is stable at said sterilizable conditions.

2. The heat-sterilizable membrane of claim 1 wherein said first hydrophobic polymer is present in said membrane in an amount of from about 1 to 30% by weight, and said second hydrophobic polymer is present in said membrane in an amount of from about 70 to 99% by weight.

3. The heat-sterilizable membrane of claim 2 wherein said first hydrophobic polymer is present in said membrane in an amount of from about 4 to 12% by weight and said second hydrophobic polymer is present in said membrane in an amount of from about 88 to 96% by weight.

4. The heat-sterilizable membrane of claim 1 wherein said second hydrophobic polymer has a vitreous transition temperature of greater than about 200° C.

5. The heat-sterilizable membrane of claim 1 wherein said first hydrophobic polymer is selected from the group consisting of partially aromatic polyamides, polycarbonate ethers, polyacrylonitriles, and cellulose triacetates.

6. The heat-sterilizable membrane of claim 5 wherein said first hydrophobic polymer comprises a partially aromatic amorphous polyamide.

7. The heat-sterilizable membrane of claim 1 wherein said second hydrophobic polymer is selected from the group consisting of polyethersulfones, polysulphones, polyetherketones, and polyaramides.

8. The heat-sterilizable membrane of claim 7 wherein said second hydrophobic polymer is selected from the group consisting of polyethersulphones and polysulphones.

9. The heat-sterilizable membrane of claim 1 wherein said first and second hydrophobic polymers are present in a molecular distribution of a particle size of up to about 1 μm.

10. A heat-sterilizable membrane comprising a first hydrophobic polymer and a second hydrophobic polymer, said first and second hydrophobic polymers normally being immiscible with each other, said first hydrophobic polymer normally being unstable when subjected to sterilization conditions comprising contact with saturated steam at about 120° C. for a period of about 20 minutes or contact with dry heat at about 180° C. for a period of about 90 minutes, and said second hydrophobic polymer normally being stable at said sterilization conditions, said first and second hydrophobic polymers being compatibilized with each other by means of an amphiphilic agent whereby said heat-sterilizable membrane is stable at said sterilization conditions.

11. The heat-sterilizable membrane of claim 10 wherein said first hydrophobic polymer is present in said membrane in an amount of from about 1 to 30% by weight, and said second hydrophobic polymer is present in said membrane in an amount of from about 7 to 99% by weight.

12. The heat-sterilizable membrane of claim 11 wherein said first hydrophobic polymer is present in said membrane in an amount of from about 4 to 12% by weight and said second hydrophobic polymer is present in said membrane in an amount of from about 88 to 96% by weight.

13. The heat-sterilizable membrane of claim 10 wherein said second hydrophobic polymer has a vitreous transition temperature of greater than about 200° C.

14. The heat-sterilizable membrane of claim 10 wherein said first hydrophobic polymer is selected from the group consisting of partially aromatic polyamides, polycarbonate ethers, polyacrylonitriles, and cellulose triacetates.

15. The heat-sterilizable membrane of claim 14 wherein said first hydrophobic polymer comprises a partially aromatic amorphous polyamide.

16. The heat-sterilizable membrane of claim 10 wherein said second hydrophobic polymer is selected from the group consisting of polyethersulfones, polysulphones, polyether ketones, and polyaramides.

17. The heat-sterilizable membrane of claim 16 wherein said second hydrophobic polymer is selected from the group selected from polyethersulphones and polysulphones.

18. The heat-sterilizable membrane of claim 10 wherein said first and second hydrophobic polymers are present in a molecular distribution of a particle size of up to about 1 $\mu$m.

19. The heat-sterilizable membrane of claim 10 including said amphiphilic agent in an amount of between about 5 and 10% by weight.

20. The heat-sterilizable membrane of claim 10 wherein said first and second hydrophobic polymers are compatibilized with each other by means of polyvinylpyrrolidone.

* * * * *

UNITED STATES PATENT AND TRADEMARK OFFICE
CERTIFICATE OF CORRECTION

PATENT NO. : 5,891,338
DATED : April 6, 1999
INVENTOR(S) : Bell et al.

It is certified that error appears in the above-identified patent and that said Letters Patent is hereby corrected as shown below:

Column 8, line 63, delete "H".

Column 8, line 65, "üls" should read --Hüls--.

Column 9, Table II, under the heading "Polymer 1","13.85" should read --13.86--.

Column 9, line 56, "sterilizable" should read --sterilization--.

Column 10, Table II, under the heading "bar. $10^{-4}$" "2.4" should read --7.4--.

Signed and Sealed this

Twenty-fourth Day of August, 1999

Attest:

Q. TODD DICKINSON

Attesting Officer

Acting Commissioner of Patents and Trademarks